United States Patent
Kishi

Patent Number: 5,624,154
Date of Patent: Apr. 29, 1997

[54] DENTAL OPERATORY CHAIR BARRIER SYSTEM

[76] Inventor: Shigeo R. Kishi, 6561 Red Coach Dr., Huntington Beach, Calif. 92647

[21] Appl. No.: 586,540

[22] Filed: Jan. 16, 1996

Related U.S. Application Data

[63] Continuation of Ser. No. 159,432, Nov. 29, 1993, abandoned.

[51] Int. Cl.⁶ .............................. A47C 7/64; A61G 15/14
[52] U.S. Cl. .................... 297/217.1; 2/114; 128/846; 128/849; 297/188.06; 297/188.2
[58] Field of Search ............................ 297/182, 188.03, 297/188.06, 188.18, 188.2, 217.1; 2/114, 912–914; 128/846, 849, 853, 856

[56] References Cited

U.S. PATENT DOCUMENTS

| | | |
|---|---|---|
| 380,602 | 4/1888 | Simmons et al. . |
| 587,616 | 8/1897 | Stuart . |
| 975,246 | 11/1910 | Johnson . |
| 2,255,973 | 9/1941 | Moobler ................................. 297/190 |
| 2,281,032 | 5/1942 | Cravetta ................................. 297/182 |
| 3,100,128 | 8/1963 | Gleitsman et al. . |
| 3,149,879 | 9/1964 | Steiber ............................. 297/188.03 |
| 4,586,196 | 5/1986 | White ......................................... 2/114 |
| 4,887,749 | 12/1989 | Kosmo et al. . |
| 4,892,239 | 1/1990 | Tomasi . |
| 4,903,710 | 2/1990 | Jessamine et al. . |
| 4,936,318 | 6/1990 | Schoolman . |
| 4,957,230 | 9/1990 | Gonzalez ........................... 297/190 X |
| 5,299,582 | 4/1994 | Potts ....................................... 128/846 |

*Primary Examiner*—Peter R. Brown
*Attorney, Agent, or Firm*—Pretty, Schroeder, Brueggemann & Clark

[57] ABSTRACT

A barrier system for dental procedures utilizing a disposable gown positioned on a dental operatory chair as a shield between dental personnel and their patients. The gown is arranged and supported on a support frame mounted to the operatory chair so that the dental personnel can easily slip into and out of the gown in moving between patients in different rooms, while the gown remains on the operatory chair.

19 Claims, 2 Drawing Sheets

DENTAL OPERATORY CHAIR BARRIER SYSTEM

This application is a continuation of application Ser. No. 08/159,432, filed Nov. 29, 1993, now abandoned.

BACKGROUND OF THE INVENTION

The present invention relates generally to dental protective devices, and more particularly, to a barrier system to protect dental personnel and their patients from cross-contamination.

The onslaught of diseases related to human immunodeficiency virus (HIV), acquired immune deficiency syndrome (AIDS), and hepatitis has changed the manner in which dentistry is delivered in dental offices and institutions. Prior to awareness of the hazards of HIV, AIDS, and hepatitis, dentists treated their patients without the use of gloves, masks, protective eyewear, or gowns. Now, the use of gloves, masks, protective eyewear, and the following of stringent sterilization techniques all are mandated by regulatory authorities, such as the Occupational Safety and Health Administration.

In the medical profession, operating procedures are generally performed in a designated operating room for a specific period of uninterrupted time. As a result, medical personnel can both scrub and change gowns before each operation.

In contrast, dental procedures usually do not involve a great amount of uninterrupted time. The dentist, dental hygienist, and dental assistants frequently leave the operatory and must go to another area of the office for supplies and so forth. Usually the dentist must also leave the operatory in order to check a hygiene patient or to see another patient undergoing dental treatment in another operatory. Dentists and their assistants who are seeing another patient usually remove their gloves and replace them with a new pair of gloves before treating the next patient. However, the gowns worn by the dentists and their assistants are usually not removed and replaced with new gowns before seeing another patient. The existing gowns may have accumulated aerosol spray from the prior patient, which may carry blood-borne or saliva-borne pathogens. This creates a risk of cross-contamination of both the operatory environment and the patients as the same gowns come into contact with them.

It will be appreciated, therefore, that there exists a need for an improved dental protective system to greatly reduce the risk of cross-contamination in the performance of dental procedures, but which will still allow dental personnel to easily move between patients. The present invention fulfills this need.

SUMMARY OF THE INVENTION

Briefly, and in general terms, the present invention resides in a barrier system utilizing a gown positioned on a dental operatory chair as a shield between the dentist and the patient. The gown is arranged and supported on the operatory chair so that the dentist can easily slip into and out of it in moving between patients in different rooms, while the gown remains on the operatory chair. The invention is also applicable to dental hygienists and assistants. As a result, the possibility of dental personnel transmitting any contamination from one patient to another patient is greatly diminished.

More specifically, one or more operatory chairs in each operatory include a support frame on which the gown is draped. The gown basically comprises a sheet of flexible material having a front portion or panel with its upper end supported on the support frame and the remainder of the gown hanging down on one side of the operatory chair. Preferably, the gown has at least partial sleeves on each side to cover the dentist's arms. The gown also may have a defined neck portion that substantially conforms to the dentist's neck. The gown further may be provided with internal reinforcement, such as a wire or the like, to better enable the gown to stand up on the support frame, particularly at the neck portion of the gown.

The support frame includes one or more upright members having a lower end mounted to an abdominal rest on the operatory chair by any suitable clamping means, and one or more cross members are joined to the upper ends of the upright members to support the gown. The upright members are preferably formed of a resilient material, permitting the upright members to bend as the dentist leans against them to get closer to the patient and to then return to their upright position when the dentist leans back. In a presently preferred embodiment, the support frame comprises two generally T-shaped supports.

The gown is removably attached to the cross members of the support frame. The gown has self-adhesive strips to attach the gown to the cross members. Alternatively, the gown can have loops formed at its upper end to be received over the cross member or hook-and-pile material to releasably attach the gown to the cross member.

Alternatively, the barrier system of the present invention can utilize a gown positioned on the patient's chair as the shield between the dentist and the patient. In this alternative embodiment, the support frame is attached to the patient's chair and supports a gown in a manner similar to that described above, so as to provide an equivalent measure of protection from cross-contamination while still allowing the the dentist to slip into and out of the gown in moving from patient to patient in different operatory rooms.

From the foregoing, it will be appreciated that the invention provides a convenient, inexpensive, and reliable barrier to contamination between dental personnel and their patients, which is effective to greatly reduce the possibility of cross-contamination of the operatory environment and patients. Other features and advantages of the present invention will be apparent from the following description of the preferred embodiment, taken in conjunction with the accompanying drawings, which illustrate, by further way of example, the principles of the invention.

DESCRIPTION OF THE PREFERRED EMBODIMENTS

Figure 1:
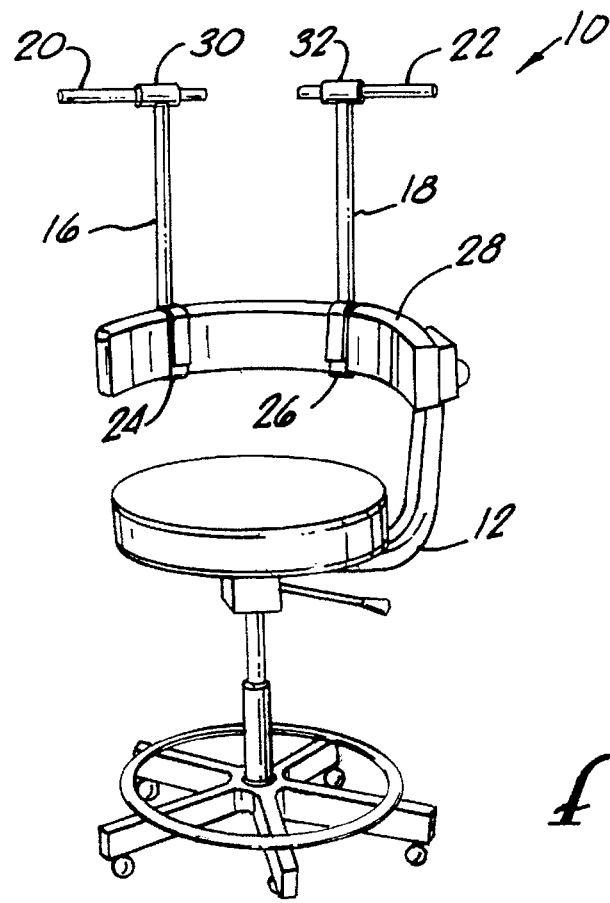
FIG. 1 is a perspective view of a support frame shown mounted on the abdominal rest of a dental operatory chair for supporting a gown, in accordance with the principles of the present invention.
Figure 2:
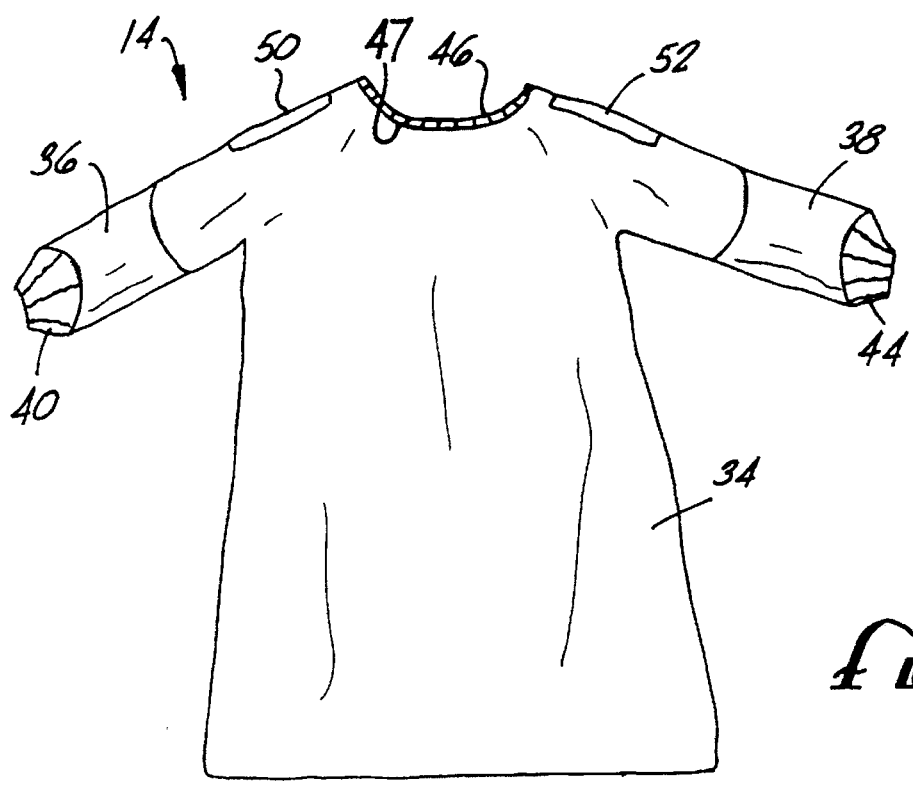
FIG. 2 is a rear view of a gown suitable for use with the support frame of FIG. 1.

Referring now to the drawings, there is shown a dental operatory chair barrier system, including a support frame indicated generally by reference numeral 10 mounted on a conventional operatory chair 12 as shown in FIG. 1. FIG. 2 illustrates a gown 14 suitable for draping on the support frame 10, in the manner illustrated in FIG. 3.

As shown in FIG. 1, the support frame 10 comprises a pair of T-shaped structures, each of which has an upright member 16, 18 and a cross member 20, 22. The upright members 16, 18 are each attached via mounting collars 24, 26 to a conventional abdominal rest 28 typically found on dental operatory chairs. Each mounting collar 24, 26 includes a split ring with a suitable strap to securely clamp the collar to the abdominal rest. The strap preferably has hook-and-pile fastening material, known by the trademark VELCRO, or the like for ease of attachment, although any suitable means for clamping the upright members 16, 18 to the abdominal rest 28 may be utilized.

The upright members 16, 18 are elongated, cylindrical shafts that are securely attached at their lower ends to the mounting collars 24, 26 so that the upright members extend essentially vertically upward from the abdominal rest 28. The shafts are preferably made out of a resilient material, such as a high impact plastic, to enable them to bend when the dentist leans against them to get closer to the patient. Because the shafts are resilient, they will then automatically return to the upright position when the dentist leans back.

The cross members 20, 22 similarly are elongated, cylindrical shafts preferably made from a resilient material such as a high impact plastic. Each cross member 20, 22 is securely received with a friction fit within a mounting sleeve 30, 32 mounted on the upper ends of each upright member 16, 18, respectively.

Referring to FIG. 2, the gown 14 includes a front portion or panel 34 that is approximately knee length. The gown 14 is open at the back. Garment sleeves 36, 38 are formed on each side of the front panel to cover at least the forearms of the dentist. The sleeves may have elastic cuffs 40, 44 for a tight fit around the dentist's gloved hands. The gown 14 includes a neck portion 46 which is curved and may be reinforced by wire or the like 47 for a snug fit and seal at the neck of the dentist.

Figure 3:
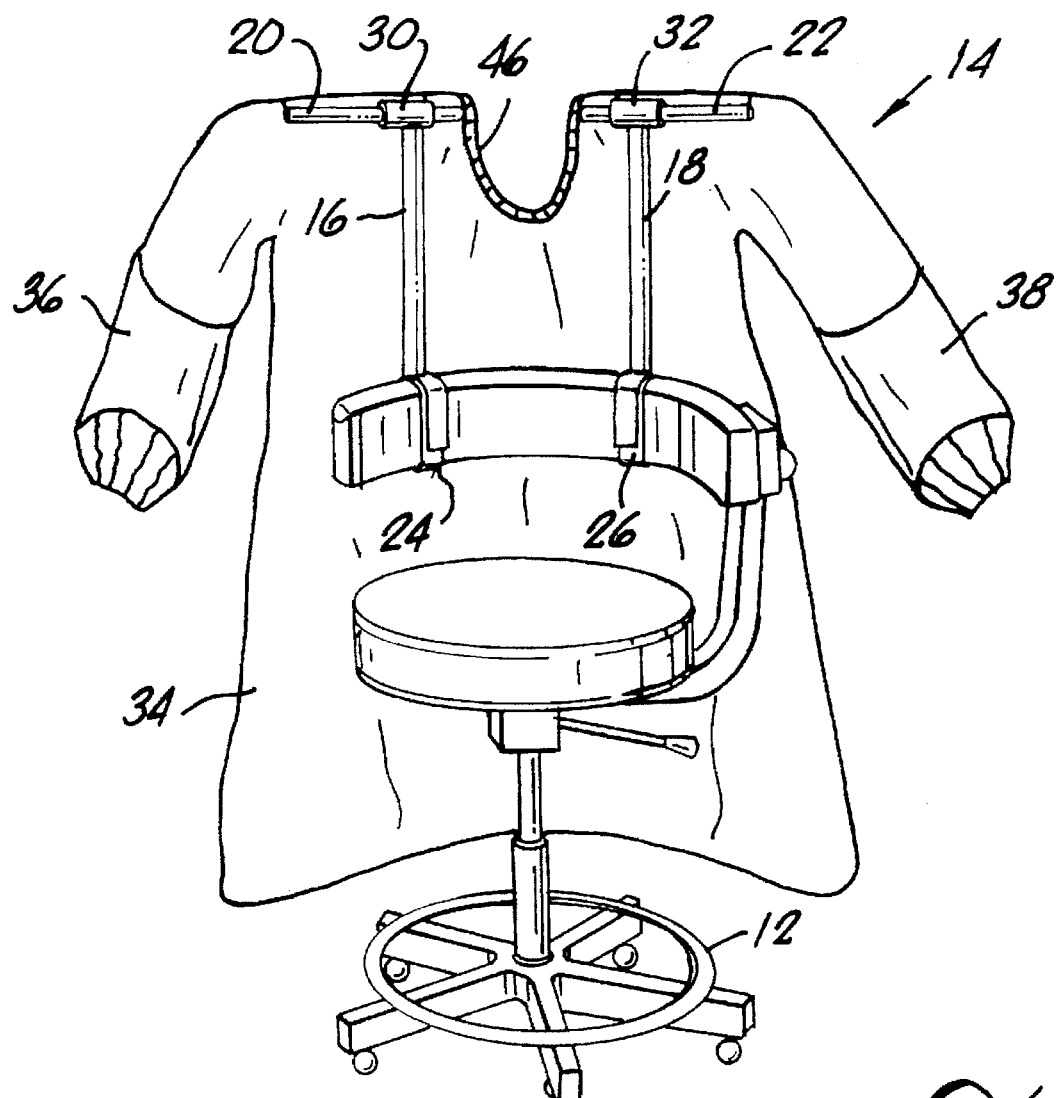
FIG. 3 is a view similar to FIG. 1, showing the gown of FIG. 2 draped on the support frame to serve as a barrier to contamination between the dentist and the patient.

Adhesive strips 50, 52 are provided near the upper edge of the gown 14 for releasably attaching it to the cross members 20, 22 of the support frame 10 (FIG. 3). Alternatively, the gown can have loops formed at its upper end to be received over the cross members, or hook-and-pile material can be used to releasably attach the gown to the cross members. The gown is made out of a flexible material which is impervious or highly resistant to penetration of moisture and infectious contaminants.

As seen in FIG. 3, in use the gown 14 is attached to the support frame 10 as described above and hangs down in front of the abdominal rest 28. As the dentist sits down in the operatory chair 12, the dentist's arms are inserted in the garment sleeves 36, 38 of the gown 14 and his or her neck is received in the neck portion 46 of the gown, with the front panel 34 of the gown forming a barrier between the dentist and the patient. When the dentist needs to leave the operatory, to attend to another patient, for example, the dentist can easily slip out of the gown 14, leaving it on the operatory chair 12 for when the dentist returns. Once the procedure with any particular patient is complete, the gown can be disposed of in the appropriate manner.

The support frame 10 for the gown 14 can be made completely adjustable. Thus, the separation of the upright members 16, 18 is adjusted simply by adjusting the positions of the mounting collars 24, 26, respectively, on the abdominal rest 28. Although not shown in the drawings, the vertical height of the upright members can be adjusted by mounting them with screws or the like to the mounting collars. The horizontal positions of the cross members 20, 22 are similarly adjustable relative to the upright members 16, 18 by sliding movement within the mounting sleeves 30, 32. It is also contemplated that the upright members could be pivotably connected to the mounting collars, and the cross members could be pivotably connected to the upright members, to allow the entire support frame to be moved out of the way during consultations with patients which do not involve the performance of dental procedures.

The present invention has been described above in terms of a presently preferred embodiment so that an understanding of the invention can be conveyed. There are, however, many configurations for a dental operatory chair barrier system not specifically described herein which utilize the principles of the present invention. The present invention should, therefore, not be seen as limited to the particular embodiments described above. All modifications, variations, or equivalent arrangements that are within the scope of the attached claims should, therefore, be considered to be within the scope of the invention.

I claim:

1. In combination with a dental operatory chair having opposing front and rear sides and a seating surface, wherein the periphery of the seating surface is substantially unobstructed on both the front and rear sides to permit dental personnel to enter the operatory chair from the rear side and to sit on the seating surface with the dental personnel's legs extending over the front side of the operatory chair, a barrier system comprising:

a support frame mounted on the operatory chair at the front side thereof, said support frame including at least one upright member and at least one cross member, said upright member having an upper end to which said cross member is attached and a lower end which is attached to the operatory chair, said upright member configured and positioned on the operatory chair with said cross member spaced above the seating surface so as to leave a substantially unobstructed space for the dental personnel's legs to extend underneath said cross member when sitting on the operatory chair facing the front side thereof; and a gown of flexible material draped on said support frame, said gown supported at an upper end on said cross member so that the remainder of said gown hangs down therefrom on the front side of the operatory chair, whereby said gown will cover at least a portion of the dental personnel's anterior when sitting on the operatory chair with the dental personnel's legs extending underneath said cross member of said support frame.

2. A barrier system as set forth in claim 1, wherein the gown further includes sleeves on opposite sides thereof, said sleeves shaped and arranged to receive the arms of a person.

3. A barrier system as set forth in claim 2, wherein the gown further includes a neck portion formed at the upper end of the gown, said neck portion shaped and arranged to substantially conform to at least a portion of the neck of a person.

4. A barrier system as set forth in claim 3, wherein the gown further includes a reinforcement member therein to help support the neck portion in an upright position on the support frame.

5. A barrier system as set forth in claim 1, wherein the gown further includes means for attaching the gown to the support frame.

6. In combination with a dental operatory chair having opposing front and rear sides and a seating surface, wherein the periphery of the seating surface is unobstructed on both the front and rear sides to permit dental personnel to enter the operatory chair from the rear side and to sit on the seating surface with the dental personnel's legs extending over the front side of the operatory chair, a barrier system comprising:

a support frame;

means for mounting said support frame on the operatory chair at the front side thereof, said support frame configured and positioned to avoid obstructing the periphery of the seating surface, whereby the dental personnel's legs are permitted to extend underneath said support frame when sitting on the operatory chair facing the front side thereof; and a gown of flexible material draped on said support frame so as to hang down therefrom on the front side of the operatory chair, whereby said gown will cover at least a portion of the dental personnel's anterior when sitting on the operatory chair with the dental personnel's legs extending underneath said support frame.

7. Apparatus as set forth in claim 6, wherein the support frame comprises an upright member formed of a resilient material permitting the upright member to bend and return to its upright position.

8. Apparatus as set forth in claim 6, wherein the dental operatory chair includes an abdominal rest positioned on the front side thereof, and the support frame includes at least one upright member mounted on the abdominal rest and at least one cross member joined to the upright member, said cross member shaped and arranged to support the gown.

9. Apparatus as set forth in claim 8, wherein the gown includes a connector at the top end thereof, said connector shaped and arranged to receive the cross member for attachment of the gown to the support frame.

10. Apparatus as set forth in claim 9, wherein the connector consists of a hook-and-pile material.

11. Apparatus as set forth in claim 9 wherein the connector consists of self-adhesive strips.

12. In combination with a dental operatory chair having opposing front and rear sides, a seating surface, and an abdominal rest located on the front side of the chair spaced above the seating surface, wherein the periphery of the seating surface is substantially unobstructed to permit dental personnel to enter the operatory chair from the rear side and to sit facing the front side thereof with the dental personnel's leg extending underneath the abdominal rest, a barrier system comprising:

a support frame including an upright member and a cross member, said upright member having an upper end and a lower end, and said cross member joined to the upright member at the upper end thereof;

means for mounting the lower end of said upright member on the abdominal rest, said mounting means positioning said support frame above the abdominal rest whereby the space below the abdominal rest remains substantially unobstructed to permit dental personnel to extend their legs when seated on the operatory chair facing the front side thereof; and a gown of flexible material having a closed front side and an open rear side and including a pair of sleeves shaped and arranged to receive the arms of a person, said gown supported at an upper end on said cross member so that the remainder of said gown hangs down therefrom on the front side of the operatory chair, whereby when dental personnel sit on the operatory chair with their legs extending through the space below the abdominal rest said gown covers substantially the entire anterior portion of the dental personnel below the neckline.

13. A method for dental personnel to protect against cross-contamination while administering to dental patients from a dental operatory chair having opposing front and rear sides and a seating surface, wherein the periphery of the seating surface is substantially unobstructed to permit dental personnel to enter the operatory chair from the rear side and to sit facing the front side thereof with the dental personnel's leg extending over the front side of the operatory chair, the method comprising:

mounting a support frame on the operatory chair at the front side thereof, said support frame including at least one upright member and at least one cross member, said upright member having an upper end to which said cross member is attached and a lower end which is attached to the operatory chair, said upright member configured and positioned on the operatory chair with said cross member spaced above the seating surface so as to leave a substantially unobstructed space for the dental personnel's legs to extend underneath said cross member when sitting on the operatory chair facing the front side thereof;

draping a gown of flexible material on said support frame, said gown supported at an upper end on said cross member so that the remainder of said gown hangs down therefrom on the front side of the operatory chair;

entering the operatory chair from the rear;

administering to a dental patient while seated on the operatory chair facing the front thereof with the dental personnel's legs extending underneath said cross member of said support frame and said gown covering at least a portion of the dental personnel's anterior; and exiting the operatory chair from the rear.

14. The method as set forth in claim 13, wherein said gown further includes sleeves on opposite sides thereof, and the arms of the dental personnel are inserted into said sleeves while administering to the dental patient.

15. The method as set forth in claim 13, wherein said gown further includes a neck portion formed at the upper end thereof, and the dental personnel's anterior is substantially covered below the neckline.

16. The method as set forth in claim 15, wherein said gown further includes a reinforcement member therein to help support said neck portion in a upright position on said support frame.

17. The method as set forth in claim 13, wherein said gown further includes a means for attaching said gown to said support frame.

18. The method as set forth in claim 13, wherein said upright member is formed of a resilient material permitting said upright member to bend and return to its upright position.

19. The method as set forth in claim 13, wherein the operatory chair includes an abdominal rest located on the front side thereof and spaced above the seating surface, said upright member is mounted on the abdominal rest, and the dental personnel's legs extend underneath the abdominal rest while administering to a dental patient.

* * * * *